(12) United States Patent
Vermeer et al.

(10) Patent No.: US 7,977,278 B2
(45) Date of Patent: *Jul. 12, 2011

(54) SUSPENSION CONCENTRATES

(75) Inventors: Ronald Vermeer, Leverkusen (DE); Peter Baur, Schondorf (DE)

(73) Assignee: Bayer Cropscience AG, Monheim (DE)

( * ) Notice: Subject to any disclaimer, the term of this patent is extended or adjusted under 35 U.S.C. 154(b) by 52 days.

This patent is subject to a terminal disclaimer.

(21) Appl. No.: 12/442,508

(22) PCT Filed: Sep. 18, 2007

(86) PCT No.: PCT/EP2007/008097
§ 371 (c)(1),
(2), (4) Date: Apr. 29, 2009

(87) PCT Pub. No.: WO2008/037375
PCT Pub. Date: Apr. 3, 2008

(65) Prior Publication Data
US 2010/0010051 A1      Jan. 14, 2010

(30) Foreign Application Priority Data
Sep. 30, 2006   (EP) ..................... 06020677

(51) Int. Cl.
*A01N 3/02*      (2006.01)
*A01N 43/40*     (2006.01)
*A01N 43/36*     (2006.01)
*A01N 57/18*     (2006.01)
*A01N 25/00*     (2006.01)

(52) U.S. Cl. .................. 504/116.1; 504/130; 504/138; 504/206; 424/405

(58) Field of Classification Search .............. None
See application file for complete search history.

(56) References Cited

U.S. PATENT DOCUMENTS

| 4,657,579 | A |   | 4/1987  | Milzner et al. |
| 4,849,432 | A |   | 7/1989  | Shiokawa et al. |
| 5,034,404 | A |   | 7/1991  | Uneme et al. |
| 5,705,476 | A |   | 1/1998  | Hoffarth |
| 6,403,529 | B1 | * | 6/2002  | Wollenweber et al. ........ 504/363 |
| 6,602,823 | B1 | * | 8/2003  | Rochling et al. ............ 504/116.1 |
| 7,407,667 | B2 | * | 8/2008  | Zerrer et al. ................... 424/405 |
| 7,838,588 | B2 | * | 11/2010 | Deroo et al. ................... 524/505 |
| 2003/0087760 | A1 |   | 5/2003  | Reekmans et al. |
| 2007/0053944 | A1 |   | 3/2007  | Vermeer |
| 2008/0312290 | A1 | * | 12/2008 | Vermeer et al. ............... 514/341 |

FOREIGN PATENT DOCUMENTS

| EP | 0539588 A1 | 5/1993 |
| EP | 0539980 | 5/1993 |
| EP | 0580533 A1 | 1/1994 |
| WO | 9830244 | 7/1998 |
| WO | 0108481 | 2/2001 |
| WO | 02089575 | 11/2002 |
| WO | 02098230 | 12/2002 |
| WO | 2005084441 | 9/2005 |
| WO | 2006111279 | 10/2006 |
| WO | WO 2006128863 A1 * | 12/2006 |

OTHER PUBLICATIONS

Kelzan® Xantham Gum ("Kelzan product brochure").*
International Search Report in PCT/EP2007/008097 dated Feb. 27, 2008 (8 pages).

* cited by examiner

*Primary Examiner* — Sreeni Padmanabhan
*Assistant Examiner* — Svetlana M Ivanova
(74) *Attorney, Agent, or Firm* — Baker Donelson Bearman, Caldwell & Berkowitz, PC

(57) ABSTRACT

The present invention relates to novel suspension concentrates of certain agrochemically active compounds, to a process for preparing these formulations and to their use for applying the active comprised therein.

15 Claims, No Drawings

SUSPENSION CONCENTRATES

CROSS REFERENCE TO RELATED APPLICATIONS

This application is a §371 National Stage Application of PCT/EP2007/008097 Sep. 18, 2007 which claims priority to European Application 06020677.8 filed Sep. 30, 2006.

BACKGROUND OF THE INVENTION

1. Field of the Invention

The present invention relates to novel suspension concentrates of certain agrochemically active compounds, to a process for preparing these formulations and to their use for applying the active compounds comprised therein.

2. Description of Related Art

To unfold their biological action, systemic agrochemically active compounds, in particular systemic insecticides and fungicides, require a formulation which allows the active compounds to be taken up by the plant/the target organisms. Accordingly, systemic agrochemically active compounds are usually formulated as an emulsion concentrate (EC), as a soluble liquid (SL) and/or as an oil-based suspension concentrate (OD). In an EC formulation and in an SL formulation, the active compound is present in dissolved form; in an OD formulation, the active compound is present as a solid. In general, a suspension concentrate (SC) is technically also feasible. However, to achieve a satisfactory biological action when using SC formulations, it is necessary for the active compound in the SC to be combined with an adjuvant. In this context, an adjuvant is a component which improves the biological action of the active compound, without the component for its part having a biological action. In particular, an adjuvant permits/facilitates the uptake of the active compound into the leaf. An adjuvant may be incorporated into the formulation of the agrochemically active compound (in-can formulation) or be added after dilution of the concentrated formulation of the spray liquor (tank-mix). To avoid dosage errors and to improve user safety during application of agrochemical products, it is advantageous to incorporate the adjuvants into the formulation. This also avoids the unnecessary use of additional packaging material for the tank-mix products.

Some water-based suspension concentrates of agrochemically active compounds comprising adjuvants are already known. Thus, WO 05/036963 describes formulations of this type which, in addition to certain fungicides, also comprise at least one penetrant from the group of the alkanolethoxylates. WO 99/060851 describes various alkanolethoxylates based on fatty alcohols.

The use of polyglycerols in certain formulations is also known. Thus, WO 98/30244 describes polyglycerol as a component of pharmaceutical compositions. WO 01/08481 discloses the use of polyglycerols in agrochemical compositions. EP 0 539 980 likewise discloses the use of polyglycerols as a component of agrochemical compositions. However, in this publication the polyglycerols according to the invention are not disclosed explicitly, and a synergism with penetrants of other classes of substances is likewise not described. Rather, the polyglycerols in question are alkoxylated polyglycerols whose structure differs considerably from that of the polyglycerols according to the invention. WO 02/089575 discloses the polyglycerols according to the invention and their use in agrochemical preparations. In this publication, a synergism with penetrants is neither disclosed nor suggested.

A disadvantage of the formulations, mentioned above, with additives is the fact that, although the biological action has been improved considerably, the activity of these formulations is weaker than that of sprayable compositions obtainable by diluting corresponding emulsion concentrates with water.

SUMMARY OF THE INVENTION

It is an object of the present invention to develop highly active, stable, storable, water-based suspension concentrates which, compared to the known formulations, improve the uptake of the active compound via the cuticles.

It has been found that this object is achieved by water-dispersible agrochemical formulations comprising a penetrant in combination with an adjuvant from the group of the polyglycerols or polyglycerol derivatives. Accordingly, the present invention provides water-dispersible agrochemical formulations, comprising

- at least one systemic agrochemically active compound which is solid at room temperature,
- at least one penetrant,
- at least one adjuvant from the group of the polyglycerols or polyglycerol derivatives obtainable by copolymerization of
  - a) glycerol,
  - b) phthalic acid and
  - c) at least one monocarboxylic acid,
- at least one nonionic surfactant and/or at least one anionic surfactant and
- optionally one or more additives from the groups of the antifreeze agents, the antifoams, the preservatives, the antioxidants, the spreading agents, the colorants and/or a thickener.

DETAILED DESCRIPTION OF A PREFERRED EMBODIMENT

In the present context, suitable penetrants are all those water-soluble/water-miscible substances which are usually employed to improve penetration of agrochemically active compounds into plants. In this context, penetrants are defined in that they penetrate from the aqueous spray liquor and/or the spray coating into the cuticles of the plant, thus being able to increase the mobility of active compounds in the cuticles. The method described below and in the literature (Baur et al., 1997, Pesticide Science 51, 131-152) may be used for determining this property.

Furthermore, it has been found that the water-based suspension concentrates according to the invention can be prepared by mixing

- at least one systemic agrochemically active compound which is solid at room temperature,
- at least one penetrant,
- at least one adjuvant from the group of the polyglycerols or polyglycerol derivatives obtainable by copolymerization of
  - a) glycerol,
  - b) phthalic acid and
  - c) at least one monocarboxylic acid,
- at least one nonionic surfactant and/or at least one anionic surfactant and
- optionally one or more additives from the groups of the antifreeze agents, the antifoams, the preservatives, the antioxidants, the spreading agents, the colorants and/or a thickener and optionally subsequently grinding the suspension formed.

Finally, it has been found that the suspension concentrates according to the invention are highly suitable for applying the agrochemically active compounds comprised therein to plants and/or their habitat.

It is extremely surprising that the suspension concentrates according to the invention exhibit an activity that is improved compared to that of sprayable compositions obtainable by diluting corresponding emulsion concentrates with water.

Furthermore, it is very surprising that the use of penetrants in combination with the adjuvants according to the invention from the group of the polyglycerols or polyglycerol derivatives results in a synergistic action.

Finally, it is extremely surprising that the suspension concentrates according to the invention have very good stability. The penetrants used, like the dispersants of a water-based suspension concentrate, have surfactant properties, which normally results in a competition with the dispersants. Especially at high storage temperature or after storage at changing temperature conditions, this results in a destabilisation of the suspension concentrate.

Preferred embodiments of the subject of the invention are described below.

Active compounds suitable for use in the formulations according to the invention are all agrochemically active compounds which are solid at room temperature.

Preference is given to systemic fungicides and insecticides.

Particular preference is given to the following fungicides:

Inhibitors of Nucleic Acid Synthesis benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid Inhibitors of Mitosis and Cell Division benomyl, carbendazim, diethofencarb, fuberidazole, thiabendazole, thiophanate-methyl Inhibitors of Respiratory Chain Complex II boscalid, carboxin, fenfuram, flutolanil, furametpyr, furmecyclox, mepronil, oxycarboxin Inhibitors of Respiratory Chain Complex III azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin Inhibitors of ATP Production fentin acetate, fentin chloride, fentin hydroxide Inhibitors of Amino Acid Biosynthesis and Protein Biosynthesis andoprim, cyprodinil, kasugamycin, kasugamycin hydrochloride hydrate, pyrimethanil Inhibitors of Signal Transduction fludioxonil, quinoxyfen Inhibitors of Lipid and Membrane Synthesis chlozolinate, iprodione, procymidone, vinclozoline
ampropylfos, potassium-ampropylfos, edifenphos, etridiazole, iprobenfos (IBP), isoprothiolane, pyrazophos
biphenyl
iodocarb, propamocarb, propamocarb hydrochloride, propamocarb-fosetylate Inhibitors of Ergosterol Biosynthesis azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidole, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefuraxoate, prochloraz, propiconazole, prothioconazole, pyrifenox, simeconazole, tebuconazole, tetraconazole, triadimefon, triadimenol, triflumizole, triforine, triticonazole, uniconazole, voriconazole, viniconazole,
aldimorph, dodemorph, dodemorph acetate, fenpropidin, fenpropimorph, spiroxamine, tridemorph,
naftifine, terbinafine Inhibitors of Cell Wall Synthesis benthiavalicarb, dimethomorph, flumorph, iprovalicarb, mandipropamid, polyoxins, polyoxorim Inhibitors of Melanin Biosynthesis carpropamid, diclocymet, fenoxanil, phthalide, pyroquilon, tricyclazole Resistance Inductors acibenzolar-S-methyl, probenazole, tiadinil Further Fungicides amibromdol, benthiazole, bethoxazin, capsimycin, carvone, chloropicrin, cufraneb, cymoxanil, dazomet, debacarb, diclomezine, ferimzone, flumetover, fluopicolide, fluoroimide, fosetyl-aluminium, fosetyl-calcium, fosetyl-sodium, hexachlorobenzene, 8-hydroxyquinoline sulphate, irumamycin, methasulfocarb, metrafenone, methyl isothiocyanate, mildiomycin, natamycin, nickel dimethyl dithiocarbamate, octhilinone, oxamocarb, oxyfenthiin, pentachlorophenol and salts, 2-phenylphenol and salts, piperalin, propanosine-sodium, pyribencarb, pyrrolnitrin, tecloftalam, tecnazene, trichlamide, valiphenal, zarilamid, 2-(2-{[6-(3-chloro-2-methylphenoxy)-5-fluoropyrimidin-4-yl]oxy}phenyl)-2-(methoxyimino)-N-methylacetamide, 2-[[[[1-[3-(1-fluoro-2-phenylethyl)oxy]phenyl]ethylidene]amino]oxy]methyl]-alpha-(methoxyimino)-N-methyl-alpha-benzacetamide, cis-1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylic acid, 2,3,5,6-tetrachloro-4-(methylsulphonyl)pyridine, 2-butoxy-6-iodo-3-propylbenzopyranon-4-one, 2-chloro-N-(2,3-dihydro-1,1,3-trimethyl-1H-inden-4-yl)-3-pyridinecarboxamide, 3,4,5-trichloro-2,6-pyridinedicarbonitrile, 3,4-dichloro-N-(2-cyanophenyl)isothiazole-5-carboxamide (isotianil)

3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidine-7-amine, 5-chloro-7-(4-methylpiperidin-1-yl)-6-(2,4,6-trifluorophenyl) [1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidine-7-amine, methyl 2-[[[cyclopropyl[(4-methoxyphenyl)imino]methyl]thio]methyl]-alpha-(methoxymethylene) benzacetate, methyl 1-(2,3-dihydro-2,2-dimethyl-1H-inden-1-yl)-1H-imidazole-5-carboxylate, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-formylamino-2-hydroxy benzamide, N-(4-chloro-2-nitrophenyl)-N-ethyl-4-methylbenzenesulphonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yl oxy)phenyl]propanamide, N-(5-bromo-3-chloropyridin-2-yl)methyl-2,4-dichloronicotinamide, N-[1-(5-bromo-3-chloropyridin-2-yl)ethyl]-2,4-dichloronicotinamide, (2S)—N-[2-[4-[[3-(4-chlorophenyl)-2-propynyl]oxy]-3-methoxyphenyl]ethyl]-3-methyl-2-[(methylsulphonyl)amino]butanamide, N-{(Z)-[(cyclopropylmethoxy)imino][6-(difluoromethoxy)-2,3-difluorophenyl]methyl}-2-benzacetamide, N-{2-[1,1'-bi(cyclopropyl)-2-yl]-phenyl}-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide, N-ethyl-N-methyl-N'-{2-methyl-5-(trifluoromethyl)-4-[3-(trimethylsilyl)propoxy]phenyl}imidoformamide, O-[1-[(4-methoxyphenoxy)methyl]-2,2-dimethylpropyl]-1H-imidazole-1-carbothioic acid, 2-amino-4-methyl-N-phenyl-5-thiazolecarboxamide, 2,4-dihydro-5-methoxy-2-methyl-4-[[[[1-[3-(trifluoromethyl)phenyl]ethylidene]amino]oxy]methyl]phenyl]-3H-1,2,4-triazol-3-one (CAS No. 185336-79-2), N-(6-methoxy-3-pyridinyl)cyclopropanecarboxamide, Particular preference is furthermore given to the following insecticides:

Neonicotinoids of the formula (T) (see, for example, EP-A1-192 606, EP-A 2-580 533, EP-A 2-376 279, EP-A 2-235 725).

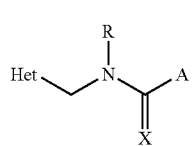

(I)

in which

Het represents a heterocycle selected from the following group of heterocycles:
2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyltetrahydrofuran-3-yl, 2-chlorothiazol-5-yl, R represents hydrogen, $C_1$-$C_6$-alkyl, $C_2$-$C_6$-alkenyl, $C_2$-$C_6$-alkynyl, —C(=O)—$CH_3$ or benzyl or together with $R^2$ represents one of the groups below:
—$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$— and X represents N—$NO_2$, N—CN or CH—$NO_2$, A represents methyl, —N($R^1$)($R^2$) or S($R^2$), in which $R^1$ represents hydrogen, $C_1$-$C_6$-alkyl, phenyl-$C_1$-$C_4$-alkyl, $C_3$-$C_6$-cycloalkyl, $C_2$-$C_6$-alkenyl or $C_2$-$C_6$-alkynyl, and $R^2$ represents $C_1$-$C_6$-alkyl, $C_2$-$C_6$-alkenyl, $C_2$-$C_6$-alkynyl, —C(=O)—$CH_3$ or benzyl.

Specific mention may be made of the following compounds (I-1) to (I-7) from the class of the neonicotinoids, where each individual compound is very particularly preferred:

(I-1) thiamethoxam
(I-2) clothianidin
(I-3) thiacloprid
(I-4) dinotefuran
(I-5) acetamiprid
(I-6) nitenpyram
(I-7) imidacloprid Active compounds from the class of the pyrethroids, for example the substances (II-1) to (II-24), where each individual compound is very particularly preferred:

(II-1) acrinathrin
(II-2) alpha-cypermethrin
(II-3) betacyfluthrin
(II-4) gamma-cyhalothrin
(II-5) cypermethrin
(II-6) deltamethrin
(II-7) esfenvalerate
(II-8) ethofenprox
(II-9) fenpropathrin
(II-10) fenvalerate
(II-11) flucythrinate
(II-12) lambda-cyhalothrin
(II-13) permethrin
(II-14) taufluvalinate
(II-15) tralomethrin
(II-16) zeta-cypermethrin
(II-17) cyfluthrin
(II-18) bifenthrin
(II-19) cyprothrin
(II-20) eflusilanate
(II-21) fubfenprox
(II-22) pyrethrin
(II-23) resmethrin
(II-24) tefluthrin Active compounds from the class of the butenolides (known from EP-A 0 539 588) of the formula (III):

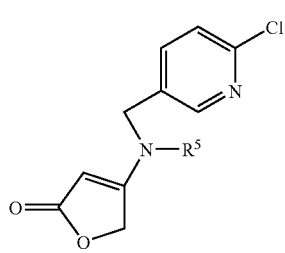

(III)

where $R^5$ represents methyl or cyclopropyl.

Specific mention may be made of the compounds (III-1) and (III-2), where each individual compound is very particularly preferred.

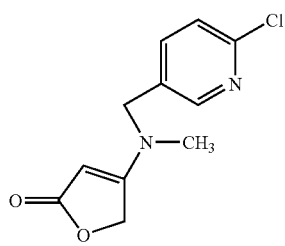

(III-1)

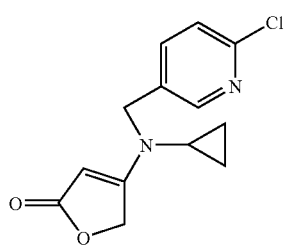

(III-2)

Active compounds from the class of the ketoenols (known from EP-A 0 539 588) of the formula (IV):

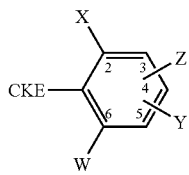

in which

W represents hydrogen, alkyl, alkenyl, alkynyl, halogen, alkoxy, halogenalkyl, halogenalkoxy or cyano, X represents halogen, alkyl, alkenyl, alkynyl, alkoxy, alkoxyalkoxy, halogenalkyl, halogenalkoxy or cyano, Y represents hydrogen, halogen, alkyl, alkenyl, alkynyl, alkoxy, cyano, halogenalkyl, halogenalkoxy or represents in each case optionally substituted phenyl or hetaryl, Z represents hydrogen, halogen, alkyl, halogenalkyl, cyano, alkoxy or halogenalkoxy, CKE represents one of the groups

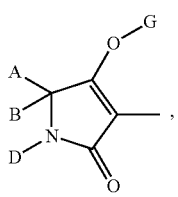

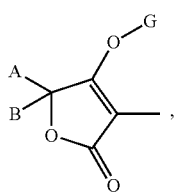

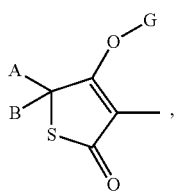

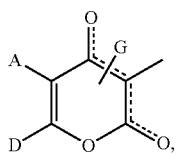

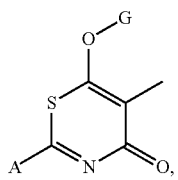

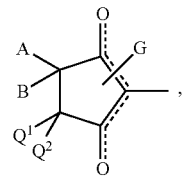

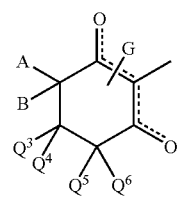

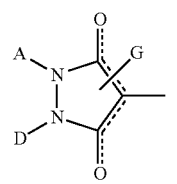

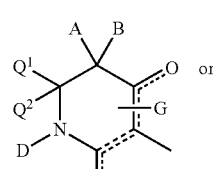

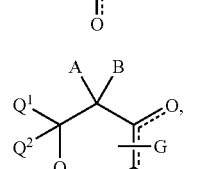

in which

A represents hydrogen, represents in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally by halogen-, alkyl-, halogenalkyl-, alkoxy-, halogenalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which is unsubstituted or substituted in the A, D moiety and optionally contains at least one (in the case of CKE=8 further) heteroatom, or A and $Q^1$ together represent alkanediyl or alkenediyl, optionally substituted by hydroxyl and/or in each case optionally substituted alkyl, alkoxy, alkylthio, cycloalkyl, benzyloxy or aryl, or D and Q¹ together with the atoms to which they are attached represent a saturated or unsaturated cycle which is unsubstituted or substituted in the D, Q¹ moiety and optionally contains at least one heteroatom, Q¹ represents hydrogen, alkyl, alkoxyalkyl, optionally substituted cycloalkyl (in which optionally one methylene group is replaced by oxygen or sulphur) or optionally substituted phenyl, Q², Q⁴, Q⁵ and Q⁶ independently of one another represent hydrogen or alkyl, Q³ represents hydrogen, represents optionally substituted alkyl, alkoxyalkyl, alkylthioalkyl, optionally substituted cycloalkyl (in which optionally one methylene group is replaced by oxygen or sulphur) or optionally substituted phenyl, or Q¹ and Q² together with the carbon atom to which they are attached represent an unsubstituted or substituted cycle which optionally contains a heteroatom, or Q³ and Q⁴ together with the carbon atom to which they are attached represent a saturated or unsaturated, unsubstituted or substituted cycle which optionally contains a heteroatom, G represents hydrogen (a) or represents one of the groups

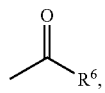
(b)

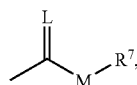
(c)

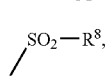
(d)

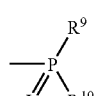
(e)

E or
(f)

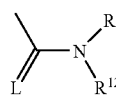
(g)

in which

E represents a metal ion equivalent or an ammonium ion,
L represents oxygen or sulphur,
M represents oxygen or sulphur,
R⁶ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
R⁷ represents in each case optionally halogen-substituted alkyl, alkenyl, alkoxyalkyl, polyalkoxyalkyl or represents in each case optionally substituted cycloalkyl, phenyl or benzyl,
R⁸, R⁹ and R¹⁰ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, R¹¹ and R¹² independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

Specific mention may be made of the compounds (IV-1) to (IV-5), where each individual compound is very particularly preferred:

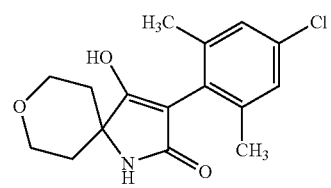
(IV-1)

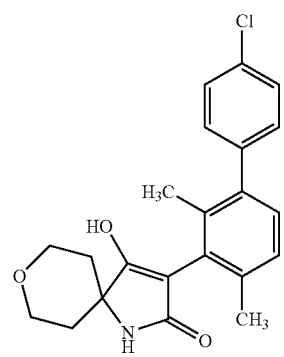
(IV-2)

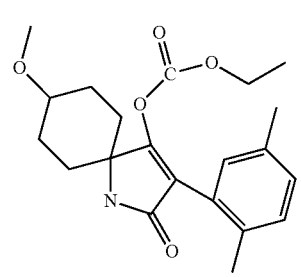
(IV-3)

spirotetramate

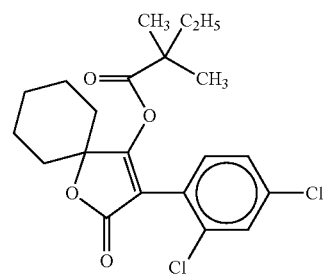
(IV-4)

spirodiclofen

-continued

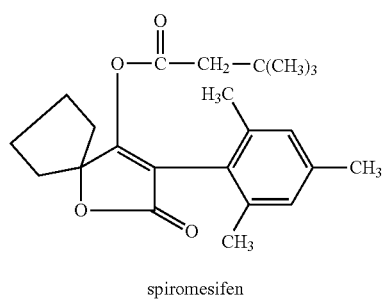
spiromesifen
(IV-5)

Active compounds from the class of the fiproles, where each individual compound is very particularly preferred:

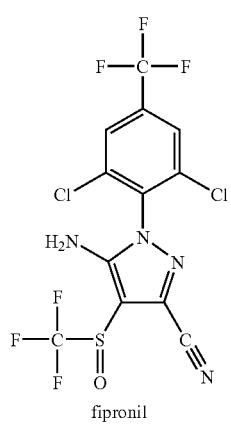
fipronil
(V-1)

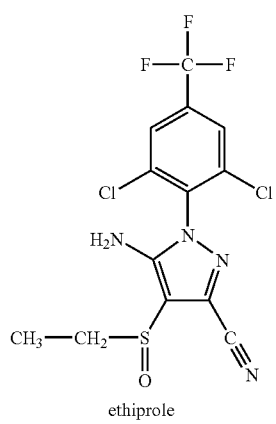
ethiprole
(V-2)

Active compounds from the class of the mectins, where each individual compound is very particularly preferred:
(VI-1) abamectin
(VI-2) emamectin
(VI-3) emamectin benzoate
(VI-4) ivermectin
(VI-5) lepimectin
(VI-6) milbemycin.

Active compounds from the class of the anthranilamides, where each individual compound is very particularly preferred:

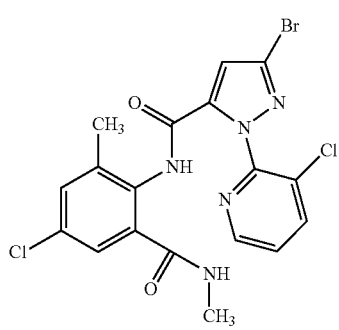
(VII-1)

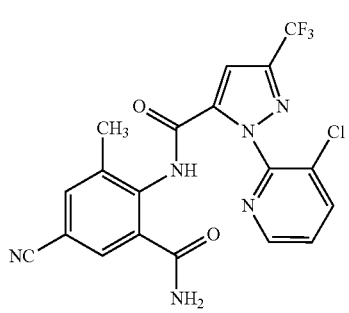
(VII-2)

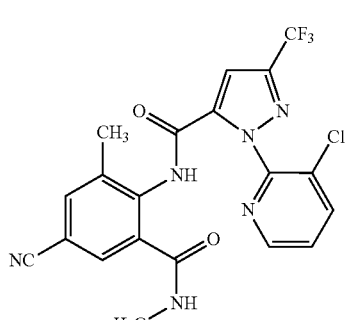
(VII-3)

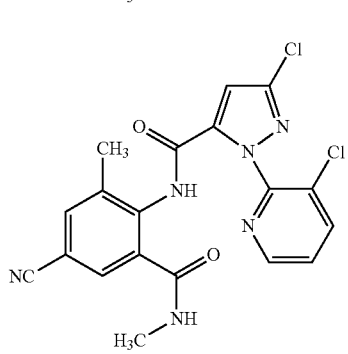
(VII-4)

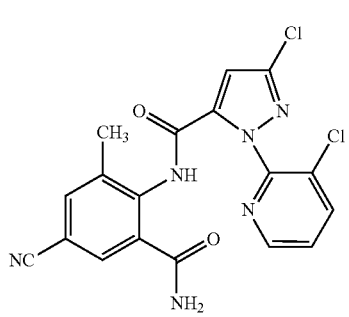
(VII-5)

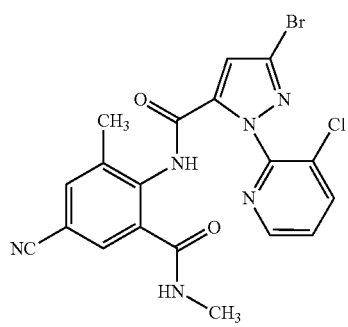
(VII-6)
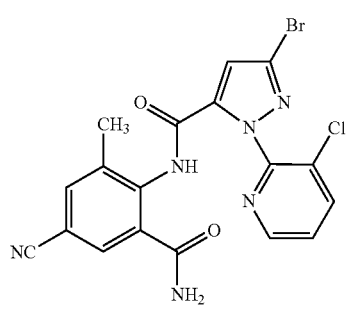
(VII-7)
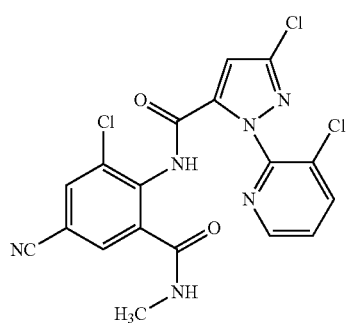
(VII-8)
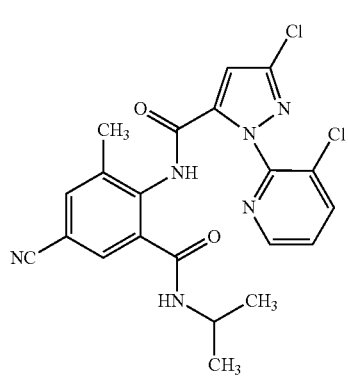
(VII-9)
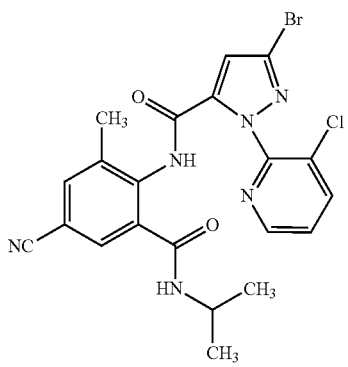
(VII-10)
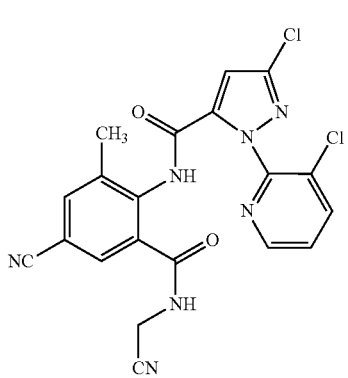
(VII-11)
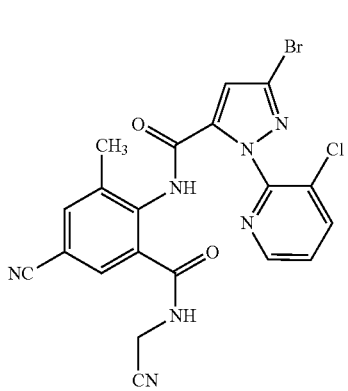
(VII-12)
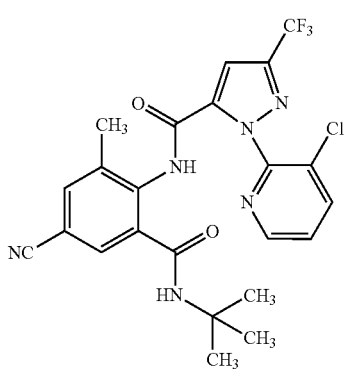
(VII-13)

-continued
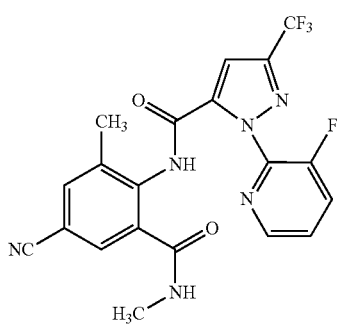
(VII-14)
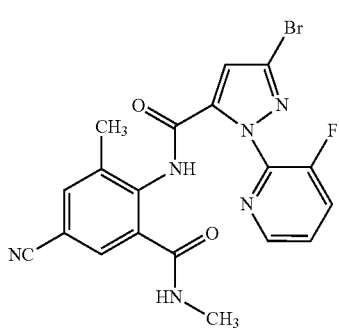
(VII-15)
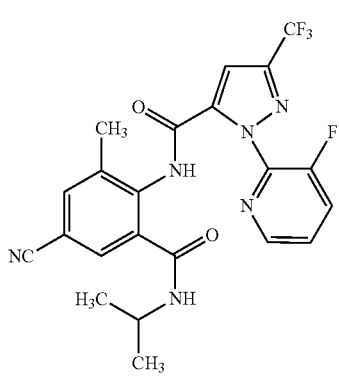
(VII-16)
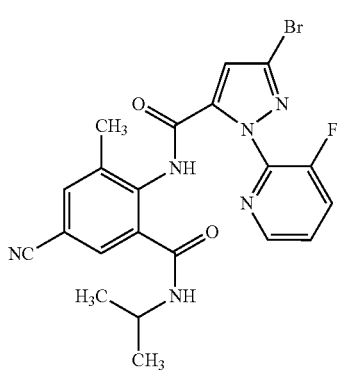
(VII-17)
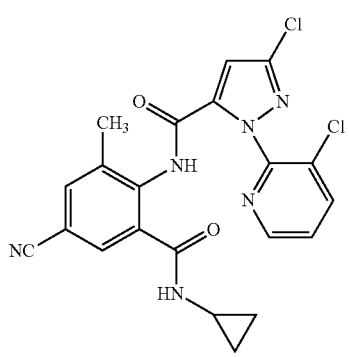
(VII-18)
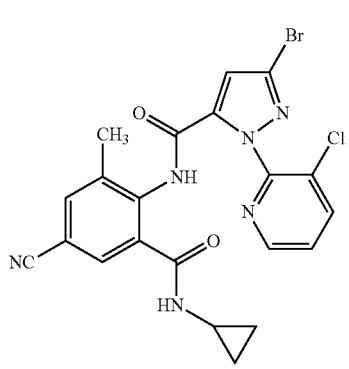
(VII-19)
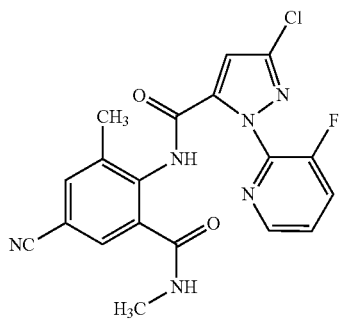
(VII-20)
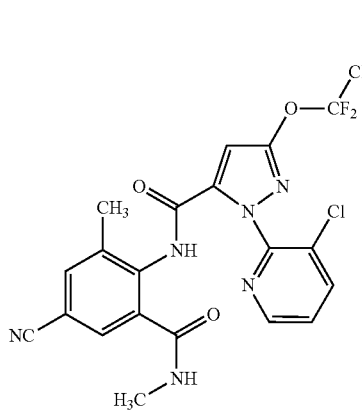
(VII-21)

-continued (VII-22)

(VII-23)

Active compounds from the class of the spinosyns, for example
(VIII-1) spinosad

Active compounds from the class of the organophosphates, for example
acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-5-methyl, demeton-5-methylsulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon and vamidothion, preferably
(IX-1) chlorpyrifos (-methyl/-ethyl),
(IX-2) cadusafos,
(IX-3) acephate,
(IX-4) fenamiphos
(IX-5) fosthiazate and
(IX-6) ethoprofos.

Active compounds from the class of the carbamates, for example alanycarb, aldicarb, aldoxycarb, allyxycarb, aminocarb, bendiocarb, benfuracarb, bufencarb, butacarb, butocarboxim, butoxycarboxim, carharyl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb and triazamate, preferably
(X-1) carbofuran,
(X-2) aldicarb and
(X-3) oxamyl.

An active compound according to the invention which is to be emphasized is imidacloprid.

An active compound according to the invention which is to be emphasized is spirotetramate.

An active compound according to the invention which is to be emphasized is thiacloprid.

In the present context, suitable penetrants are all those water-soluble/water-miscible substances which are usually employed to improve the penetration of agrochemically active compounds into plants.

Preferred penetrants are alkanolalkoxylates of the formula (XI)

$$R^3-O-(-AO)_m R^4 \quad (XI)$$

in which
$R^3$ represents straight-chain or branched alkyl having 4 to 20 carbon atoms,
$R^4$ represents H, methyl, ethyl, n-propyl, i-propyl, n-butyl, i-butyl, t-butyl, n-pentyl or n-hexyl,
AO represents an ethylene oxide radical, a propylene oxide radical, a butylene oxide radical or represents mixtures of ethylene oxide and propylene oxide radicals or butylene oxide radicals and
m represents numbers from 2 to 30.

A particularly preferred group of penetrants are alkanolalkoxylates of the formula (XI-1)

$$R^3-O-(-EO-)_n-R^4 \quad (XI-1)$$

in which
$R^3$ is as defined above,
$R^4$ is as defined above,
EO represents —$CH_2$—$CH_2$—O— and
n represents numbers from 2 to 20.

In the formulae given above,
$R^3$ preferably represents butyl, i-butyl, n-pentyl, i-pentyl, neopentyl, n-hexyl, i-hexyl, n-octyl, i-octyl, 2-ethylhexyl, nonyl, i-nonyl, decyl, n-dodecyl, i-dodecyl, lauryl, myristyl, i-tridecyl, trimethylnonyl, palmityl, stearyl or eicosyl.

A very particularly preferred group of penetrants are alkanolalkoxylates of the formula $$CH_3-(CH_2)_t-CH_2-O-(-CH_2-CH_2-O-)_u-R^4 \quad (XI-1-1)$$

in which
$R^4$ is as defined above,
t represents numbers from 6 to 13,
u represents numbers from 4 to 17.

Alkanolalkoxylates of the formula (XI-1-1-1)

$$CH_3-(CH_2)_t-CH_2-O-(-CH_2-CH_2-O-)_u-R^4 \quad (XI-1-1-1)$$

in which
$R^4$ is as defined above,
t represents the average value 10.5 and
u represents the average value 8.4
may be mentioned as being especially preferred.

Alkanolalkoxylate of the formula (XI-1-1-1)

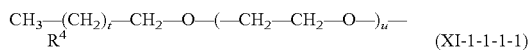
(XI-1-1-1)

in which
t represents the average value 10.5 and
u represents the average value 8.4
may be mentioned as being emphasized.

The above formulae provide a general definition of the alkanolalkoxylates. These substances are mixtures of substances of the stated type having different chain lengths. The indices therefore have average values which may also deviate from whole numbers.

The alkanolalkoxylates of the formulae indicated are known or can be prepared by known methods (cf. WO 98-35 553, WO 00-35 278 and EP-A 0 681 865).

A further group of preferred penetrants are polyalkoxytriglycerides. Polyalkoxytriglycerides can be prepared by alkoxylation of triglycerides. The alkoxylation of triglycerides gives substance mixtures in which one to three of the side chains are alkoxylated. In alkoxylations, a distinction may be made between ethoxylation, propoxylation, butoxylation or a mixture of these processes. For each of the side chains, the length of the unmodified side chains can vary from 9 to 24, preferably from 12 to 22, very preferably from 14 to 20, carbon atoms independently of the other side chains in the same molecule. These aliphatic side chains can be straight-chain or branched.

In a preferred embodiment of the present invention, the polyalkoxytriglycerides are obtained by ethoxylation of triglycerides.

In a particularly preferred embodiment of the present invention, the polyalkoxytriglycerides are obtained by ethoxylation of rapeseed oil, maize oil, palm kernel oil or almond oil.

In a very particularly preferred embodiment of the present invention, the polyalkoxytriglycerides are obtained by ethoxylation of rapeseed oil, the degree of ethoxylation being from 60 to 80% by weight.

Corresponding polyalkoxytriglycerides are known or can be prepared by known methods (commercially available, for example, under the names Crovol® A 70 UK, Crovol® CR 701, Crovol® M 70 and Crovol® PK 70 from Croda).

In the present context, suitable adjuvants are compounds from the group of the polyglycerols and polyglycerol derivatives obtainable by copolymerization of a) glycerol, b) phthalic acid and c) at least one monocarboxylic acid.

Particularly preferred monocarboxylic acids c) are saturated or unsaturated fatty acids or mixtures thereof, such as, for example, coco acid, oleic acid, lauric acid, tridecanoic acid, myristic acid, pentadecanoic acids palmitic acid, margaric acid, stearic acid, nonadecanoic acid, eicosanoic acid, docosanoic acid, linoleic acid, linolenic acid, palmitic acid and tallow fatty acid.

Very particularly preferred monocarboxylic acids c) are coco acid and tallow fatty acid.

An especially preferred monocarboxylic acid c) is coco acid.

The polyglycerol derivatives according to the invention preferably comprise from 19.9 to 99% by weight of structural units derived from glycerol, from 0.1 to 30% by weight of structural units derived from phthalic acid and from 0.9 to 80% by weight of structural units derived from the monocarboxylic acid.

The polyglycerol derivatives according to the invention particularly preferably comprise from 50 to 90% by weight of structural units derived from glycerol, from 1 to 25% by weight of structural units derived from phthalic acid and from 2 to 49% of structural units derived from the monocarboxylic acid.

Especially advantageous is a content of from 1 to 10% by weight derived from phthalic acid.

The preparation of corresponding polyglycerols is disclosed in WO 02/89575. Corresponding polyglycerols and polyglycerol derivatives are commercially available under the trade name Synergen® GL (Clariant).

Preference is given to a combination of ethoxylated triglycerides as penetrant and polyglycerols obtainable by copolymerization of a) glycerol, b) phthalic acid and c) at least one monocarboxylic acid as adjuvant.

Particular preference is given to a combination of ethoxylated rapeseed oil, maize oil, palm kernel oil or almond oil as penetrant and polyglycerols obtainable by copolymerization of a) glycerol, b) phthalic acid and c) coco acid, oleic acid, lauric acid, tridecanoic acid, myristic acid, pentadecanoic acid, palmitic acid, margaric acid, stearic acid, nonadecanoic acid, eicosanoic acid, docosanoic acid, linoleic acid, linolenic acid, palmitic acid or tallow fatty acid as adjuvant.

Very particular preference is given to a combination of ethoxylated rapeseed oil where the degree of ethoxylation is from 60 to 80% by weight as penetrant and polyglycerols obtainable by copolymerization of a) glycerol, b) phthalic acid and c) coco acid as adjuvant.

Special preference is given to a combination of ethoxylated rapeseed oil where the degree of ethoxylation is from 60 to 80% by weight as penetrant and polyglycerols comprising from 19.9 to 99% by weight of structural units derived from glycerol, from 0.1 to 30% by weight of structural units derived from phthalic acid and from 0.9 to 80% by weight of structural units derived from the monocarboxylic acid as adjuvant.

Emphasis is given to a combination of ethoxylated rapeseed oil where the degree of ethoxylation is from 60 to 80% by weight as penetrant and polyglycerols comprising from 50 to 90% by weight of structural units derived from glycerol, from 1 to 25% by weight of structural units derived from phthalic acid and from 2 to 49% of structural units derived from the monocarboxylic acid as adjuvant.

Suitable nonionic surfactants are all compounds of this type which can usually be employed in agrochemical compositions. Polyethylene oxide/polypropylene oxide block copolymers, polyethylene glycol ethers of straight-chain alcohols, reaction products of fatty acids with ethylene oxide and/or propylene oxide, furthermore polyvinyl alcohol, polyvinylpyrrolidone, mixed polymers of polyvinyl alcohol and polyvinylpyrrolidone, mixed polymers of polyvinyl acetate and polyvinylpyrrolidone and also copolymers of (meth)acrylic acid and (meth)acrylic esters, furthermore alkyl ethoxylates and alkylaryl ethoxylates which may optionally be phosphated and may optionally be neutralized with bases, polyoxyamine derivatives and nonylphenol ethoxylates may be mentioned as being preferred.

Suitable anionic surfactants are all substances of this type which can usually be employed in agrochemical compositions. Preference is given to alkali metal and alkaline earth metal salts of alkylsulphonic acids or alkylarylsulphonic acids.

A further preferred group of anionic surfactants or dispersants are salts of polystyrenesulphonic acids, salts of polyvinylsulphonic acids, salts of naphthalenesulphonic acid/formaldehyde condensates, salts of condensates of naphthalenesulphonic acid, phenolsulphonic acid and formaldehyde and also salts of lignosulphonic acid.

Suitable antifoams are all substances which can usually be employed for this purpose in agrochemical compositions. Preference is given to silicone oils and magnesium stearate.

Suitable antioxidants are all substances which can usually be employed for this purpose in agrochemical compositions. Preference is given to butylated hydroxytoluene (2,6-di-t-butyl-4-methylphenol, BHT).

Suitable colorants are all substances which can usually be employed for this purpose in agrochemical compositions. Examples which may be mentioned are titanium dioxide, carbon black, zinc oxide and blue pigments and also permanent red FGR.

Suitable preservatives are all substances of this type which can usually be employed for this purpose in agrochemical compositions. Examples which may be mentioned are Preventol® (from Bayer AG) and Proxel®.

Suitable spreading agents are all substances which can usually be employed for this purpose in agrochemical compositions. Preference is given to polyether- or organo-modified polysiloxanes.

Suitable antifreeze agents are all substances of this type which can usually be employed in agrochemical compositions. Preference is given to urea, glycerol and propylene glycol.

Suitable thickeners are all substances of this type which can usually be employed in agrochemical compositions. Preference is given to silicates (such as, for example, Attagel® 50 from Engelhard) or xanthan gum (such as, for example, Kelzan® S from Kelko).

The compositions according to the invention comprise
in general from 1 to 60% by weight of one or more of the agrochemically active compounds which may be used according to the invention, preferably from 5 to 50% by weight and particularly preferably 10 to 30% by weight.
in general from 1 to 50% by weight of at least one penetrant according to the invention, preferably from 2 to 30% by weight and particularly preferably from 5 to 20% by weight.
in general from 1 to 25% by weight of at least one adjuvant according to the invention, preferably from 2 to 15% by weight and particularly preferably 5 to 10% by weight.
in general from 1 to 20% by weight of at least one nonionic and/or at least one anionic surfactant, preferably from 2.5 to 10% by weight.
in general from 0.1 to 25% by weight of additives from the groups of the antifoams, the preservatives, the antioxidants, the spreading agents, the colorants and/or the thickeners, preferably from 0.1 to 20% by weight.

The suspension concentrates according to the invention are prepared by mixing the particular ratios desired of the components with one another. The components may be mixed with one another in any order. Expediently, the solid components are employed in a finely ground state. However, it is also possible to subject the suspension formed after mixing of the components initially to a coarse grinding then to a fine grinding so that the mean particle size is below 20 µm. Preferred are suspension concentrates in which the solid particles have a mean particle size of from 1 to 10 µm.

When carrying out the process according to the invention, the temperatures may be varied within a certain range. In general, the process is carried out at temperatures between 10° C. and 60° C., preferably between 15° C. and 40° C.

Suitable for carrying out the process according to the invention are customary mixers and grinders employed for producing agrochemical formulations.

The compositions according to the invention are formulations which are stable even after prolonged storage at elevated temperatures or in the cold, since no crystal growth is observed. By dilution with water, they can be converted into homogeneous spray liquors.

The application rate of the compositions according to the invention can be varied within a relatively wide range. It depends on the agrochemically active compounds in question and their content in the compositions.

The compositions of the invention, which comprise at least one insecticidally active compound, in combination with good plant tolerance, favourable toxicity to warm-blooded animals and high compatibility with the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterohius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is further possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., Pentomidae, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helicbrysii*, *Brachycolus* spp., *Brevicoryne brassicae*, *Calligypona marginata*, *Carneocephala fulgida*, *Ceratovacuna lanigera*, Cercopidae, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compositions according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms).

The compositions of the invention can in addition to the abovementioned agrochemically active compounds comprise other active compounds as mixing partners, such as insecticides, attractants, sterilants, bactericides, acaricides, nematicides, fungicides, growth-regulating substances, herbicides, safeners, fertilizers or semiochemicals.

Particularly favourable mixing partners are, for example, the following components:
Fungicides:
Inhibitors of Mitosis and Cell Division
ethaboxam, pencycuron, zoxamide
Inhibitors of Respiratory Chain Complex I
diflumetorim
Inhibitors of Respiratory Chain Complex II
penthiopyrad, thifluzamid
Decouplers
dinocap, fluazinam
Inhibitors of ATP Production
silthiofam
Inhibitors of Amino Acid Biosynthesis and Protein Biosynthesis
blasticidin-S, mepanipyrim
Inhibitors of Signal Transduction
fenpiclonil,
Inhibitors of Lipid and Membrane Synthesis
tolclofos-methyl
Inhibitors of Ergosterol Biosynthesis
fenhexamid,
Inhibitors of Cell Wall Synthesis
validamycin A
Multisite
captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Further Fungicides
chinomethionat, chloropicrin, cyflufenamid, dichlorophen, dicloran, diphenylamine, nitrothal-isopropyl, proquinazid, quintozene, triazoxide,
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
Sodium Channel Modulators/Voltage-Dependent Sodium Channel Blockers
Pyrethroids,
for example allethrin (d-cis-trans, d-trans), bioallethrin, bioallethrin S-cyclopentyl isomer, bioethano-methrin, biopermethrin, bioresmethrin, chlovaporthrin, cis-cypermethrin, cis-resmethrin, cis-permethrin, clocythrin, cyhalothrin, cyphenothrin, empenthrin (1R isomer), fenfluthrin, fenpyrithrin, flubrocythrinate, flufenprox, flumethrin, fluvalinate, imiprothrin, kadethrin, metofluthrin, permethrin (cis-, trans-), phenothrin (1R-trans isomer), prallethrin, profluthrin, protrifenbute, pyresmethrin, RU 15525, silafluofen, terallethrin, tetramethrin (1R isomer), transfluthrin, ZXI 8901, DDT
oxadiazines,
for example indoxacarb
semicarbazones,
for example metaflumizone (BAS3201)
Acetylcholine Receptor Agonists/Antagonists
chloronicotinyls,
for example nithiazine
nicotine, bensultap, cartap
Acetylcholine Receptor Modulators
Spinosyns,
for example spinosad, spinetoram
GABA-Controlled Chloride Channel Antagonists
organochlorines,
for example camphechlor, chlordane, endosulfan, gamma-HCH, HCH, heptachlor, lindane, methoxychlor
fiproles,
for example acetoprole, ethiprole, fipronil, pyrafluprole, pyriprole, vaniliprole
juvenile hormone mimetics,
for example diofenolan, epofenonane, fenoxycarb, hydroprene, kinoprene, methoprene, pyriproxifen, triprene
Ecdysone Agonists/Disruptors
diacylhydrazines,
for example chromafenozide, halofenozide, methoxyfenozide, tebufenozide
Chitin Biosynthesis Inhibitors
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine
Oxidative Phosphorylation Inhibitors, ATP Disruptors
diafenthiuron
organotin compounds,
for example azocyclotin, cyhexatin, fenbutatin oxide
Oxidative Phosphorylation Decouplers Acting by Interrupting the H-Proton Gradient
pyrroles,
for example chlorfenapyr
dinitrophenols,
for example binapacyrl, dinobuton, dinocap, DNOC, meptyldinocap
Site-I Electron Transport Inhibitors
METIs,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Lipid Synthesis Inhibitors
Tetramic acids,
for example cis-3-(2,5-dimethylphenyl)-4-hydroxy-8-methoxy-1-azaspiro[4.5]dec-3-en-2-one
Carboxamides,
for example flonicamid
Octopaminergic agonists,
for example amitraz
Inhibitors of Magnesium-Stimulated ATPase,
propargite Nereistoxin analogues,
for example thiocyclam hydrogen oxalate, thiosultap-sodium
Ryanodine receptor agonists,
Benzodicarboxamides,
for example flubendiamid
Biologicals, Hormones or Pheromones
  Azadirachtin, *Bacillus* spec., *Beauveria* spec., *Codlemone*, *Metarrhizium* spec., *Paecilomyces* spec., *Thuringiensin*, *Verticillium* spec.
Active compounds with unknown or unspecific mechanisms of action
  fumigants,
for example aluminium phosphide, methyl bromide, sulphuryl fluoride
  antifeedants,
for example cryolite, flonicamid, pymetrozine
  mite growth inhibitors,
for example clofentezine, etoxazole, hexythiazox
  amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, di-cyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the compositions according to the invention can furthermore be present in their commercially available formulations and in the use forms, prepared from these formulations, as a mixture with synergistic agents. Synergistic agents are compounds which increase the action of the active compounds present in the compositions according to the invention, without it being necessary for the synergistic agent added to be active itself.

When used as insecticides, the compositions according to the invention can furthermore be present in their commercially available formulations and in the use forms, prepared from these formulations, as mixtures with inhibitors which reduce degradation of the agrochemically active compound present after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional breeding and optimization methods or by biotechnological and genetic engineering methods or by combinations of these methods, including the transgenic plants and including the plant cultivars which can or cannot be protected by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds, as well as roots, tubers and rhizomes. The plant parts also include harvested material, and vegetative and generative propagation material, for example cuttings, tubers, rhizomes, offshoots and seeds.

Treatment according to the invention of the plants and plant parts with the compositions is carried out directly or by action on their environment, habitat or storage space using customary treatment methods, for example by dipping, spraying, evaporating, atomizing, broadcasting, spreading-on, injecting and, in the case of propagation material, in particular in the case of seeds, furthermore by coating with one or more layers.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compositions according to the invention. The preferred ranges stated above for the compositions also apply to the treatment of these plants. Particular emphasis is given to the treatment of plants with the compositions specifically mentioned in the present text.

The compositions according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compositions according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the compositions according to the invention.

The compositions according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the compositions can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compositions according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis,*

*Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood, processed wood products and coating compositions.

The ready-to-use compositions may, if appropriate, comprise further insecticides and, if appropriate, one or more fungicides.

With respect to possible additional mixing partners, reference may be made to the insecticides and fungicides mentioned above.

The compositions according to the invention can likewise be employed for protecting objects which come into contact with seawater or brackish water, in particular hulls, screens, nets, buildings, moorings and signalling systems, against fouling.

Furthermore, the compositions according to the invention, alone or in combinations with other active compounds, may be employed as antifouling agents.

In domestic, hygiene and stored-product protection, the compositions are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

When the compositions according to the invention comprise at least one fungicidally active compound, they have very good fungicidal properties and can be used for controlling phytopathogenic fungi, such as Plasmodiophoromycetes, Oomycetes, Chytridiomycetes, Zygomycetes, Ascomycetes, Basidiomycetes, Deuteromycetes, etc.

Some pathogens causing fungal diseases which come under the generic names listed above may be mentioned as examples, but not by way of limitation:

Diseases caused by powdery mildew pathogens, such as, for example,

*Blumeria* species, such as, for example, *Blumeria graminis; Podosphaera* species, such as, for example, *Podosphaera leucotricha;*

*Sphaerotheca* species, such as, for example, *Sphaerotheca fuliginea;*

*Uncinula* species, such as, for example, *Uncinula necator;*

Diseases caused by rust disease pathogens, such as, for example,

*Gymnosporangium* species, such as, for example, *Gymnosporangium sabinae*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondite* or *Puccinia triticina;*

*Uromyces* species, such as, for example, *Uromyces appendiculatus;*

Diseases caused by pathogens from the group of the Oomnycetes, such as, for example,

*Bremia* species, such as, for example, *Bremia lactucae;*

*Peronospora* species, such as, for example, *Peronospora pisi* or *P. brassicae;*

*Phytophthora* species, such as, for example *Phytophthora infestans;*

*Plasmopara* species, such as, for example, *Plasmopara viticola;*

*Pseudoperonospora* species, such as, for example, *Pseudoperonospora humuli* or *Pseudoperonospora cubensis;*

*Pythium* species, such as, for example, *Pythium ultimum;*

Leaf blotch diseases and leaf wilt diseases caused, for example, by

*Alternaria* species, such as, for example, *Alternaria solani;*

*Cercospora* species, such as, for example, *Cercospora beticola;*

*Cladiosporium* species, such as, for example, *Cladiosporium cucumerinum;*

*Cochliobolus* species, such as, for example, *Cochliobolus sativus* (conidia form: *Drechslera*, Syn: *Helminthosporium*);

*Colletotrichum* species, such as, for example, *Colletotrichum lindemuthanium;*

*Cycloconium* species, such as, for example, *Cycloconium oleaginum;*

*Diaporthe* species, such as, for example, *Diaporthe citri;*

*Elsinoe* species, such as, for example, *Elsinoe fawcettii;*

*Gloeosporium* species, such as, for example, *Gloeosporium laeticolor;*

*Glomerella* species, such as, for example, *Glomerella cingulata;*

*Guignardia* species, such as, for example, *Guignardia bidwelli;*

*Leptosphaeria* species, such as, for example, *Leptosphaeria maculans;*

*Magnaporthe* species, such as, for example, *Magnaporthe grisea;*

*Mycosphaerella* species, such as, for example, *Mycosphaerella graminicola;*

*Phaeosphaeria* species, such as, for example, *Phaeosphaeria nodorum;*

*Pyrenophora* species, such as, for example, *Pyrenophora teres;*

*Ramularia* species, such as, for example, *Ramularia collocygni;*

*Rhynchosporium* species, such as, for example, *Rhynchosporium secalis;*

*Septoria* species, such as, for example, *Septoria apii;*

*Typhula* species, such as, for example, *Typhula incarnata;*

*Venturia* species, such as, for example, *Venturia inaequalis;*

Root and stem diseases caused, for example, by

*Corticium* species, such as, for example, *Corticium graminearum;*

*Fusarium* species, such as, for example, *Fusarium oxysporum;*

*Gaeumannomyces* species, such as, for example, *Gaeumannomyces graminis;*

*Rhizoctonia* species, such as, for example *Rhizoctonia solani;*

*Tapesia* species, such as, for example, *Tapesia acuformis;*

*Thielaviopsis* species, such as, for example, *Thielaviopsis basicola;*

Ear and panicle diseases (including maize cobs) caused, for example, by

*Alternaria* species, such as, for example, *Alternaria* spp.;

*Aspergillus* species, such as, for example, *Aspergillus flavus;*

*Cladosporium* species, such as, for example, *Cladosporium* spp.;

*Claviceps* species, such as, for example, *Claviceps purpurea;*

*Fusarium* species, such as, for example, *Fusarium culmorum;*

*Gibberella* species, such as, for example, *Gibberella zeae;*

*Monographella* species, such as, for example, *Monographella nivalis;*

Diseases caused by smut fungi, such as, for example,

*Sphacelotheca* species, such as, for example, *Sphacelotheca reiliana;*

*Tilletia* species, such as, for example, *Tilletia caries;*

*Urocystis* species, such as, for example, *Urocystis occulta;*

*Ustilago* species, such as, for example, *Ustilago nuda;*

Fruit rot caused, for example, by

*Aspergillus* species, such as, for example, *Aspergillus flavus;*

*Botrytis* species, such as, for example, *Botrytis cinerea;*

*Penicillium* species, such as, for example, *Penicillium expansum;*

*Sclerotinia* species, such as, for example, *Sclerotinia sclerotiorum;*

*Verticilium* species, such as, for example, *Verticilium alboatrum;*

Seed- and soil-borne rot and wilt diseases, and also diseases of seedlings, caused, for example, by

*Fusarium* species, such as, for example, *Fusarium culmorum;*

*Phytophthora* species, such as, for example, *Phytophthora cactorum;*

*Pythium* species, such as, for example, *Pythium ultimum;*

*Rhizoctonia* species, such as, for example, *Rhizoctonia solani;*

*Sclerotium* species, such as, for example, *Selerotium rolfsii;*

Cancerous diseases, galls and witches' broom caused, for example, by

*Nectria* species, such as, for example, *Nectria gailigena;*

Wilt diseases caused, for example, by

*Monilinia* species, such as, for example, *Monilinia laxa;*

Deformations of leaves, flowers and fruits caused, for example, by

*Taphrina* species, such as, for example, *Taphrina deformans;*

Degenerative diseases of woody plants caused, for example, by

*Esca* species, such as, for example, *Phaemonielia clamydospora;*

Diseases of flowers and seeds caused, for example, by

*Botrytis* species, such as, for example, *Botrytis cinerea;*

Diseases of plant tubers caused, for example, by

*Rhizoctonia* species, such as, for example, *Rhizoctonia solani;*

Diseases caused by bacteriopathogens, such as, for example,

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora.*

Preference is given to controlling the following diseases of soya beans:

fungal diseases on leaves, stems, pods and seeds caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllosticta leaf spot (*Phyllosticta sojaecola*), powdery mildew (*Miciosphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base caused, for example, by
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The preparation and use examples below illustrate the invention without limiting it in any way.

Preparation Examples

To prepare a suspension concentrate, initially all liquid components are mixed with one another. In the next step, the solids are added and the mixture is stirred until a homogeneous suspension is formed. The homogeneous suspension is subjected initially to coarse grinding and then to fine grinding, resulting in a suspension in which 90% of the solids particles have a particle size below 10 µm. Subsequently, Kelzan® S and water are added at room temperature with stirring. This gives a homogeneous suspension concentrate.

TABLE 1

Compositions of formulations according to the invention (in % by weight)

| | Example | | | | | | | | | |
|---|---|---|---|---|---|---|---|---|---|---|
| | 1 | 2 | 3 | 4 | 5 | 6 | 7 | 8 | 9 | 10 |
| Imidacloprid | 18.7 | 18.7 | | | 18.7 | 31.3 | 31.3 | | 4.4 | 10.6 |
| Spirotetramate | | | 18.7 | | | | | | 4.4 | 10.6 |
| Thiacloprid | | | | 18.7 | | | | 22.2 | | |
| Crovol ® CR 70 G | 10 | 15 | 10 | 10 | | 7.5 | 10 | 10 | 20 | 15 |
| Cenapol ® C 100 | | | | | 7.5 | | | | | |
| Synergen ® GL 5 | 5 | 5 | 5 | 5 | 5 | 5 | 5 | 5 | 5 | 5 |
| Glycerol | 5 | 5 | 5 | 5 | 5 | | | | 5 | 5 |
| Emulgator PS 29 | 4 | 4 | 4 | 4 | 4 | | | | | |
| Atlox ® 4913 | | | | | | 4.5 | 4.5 | 4.5 | 3 | 3 |
| Emulgator PS 54 | | | | | | 1.5 | 1.5 | 1.5 | 3 | 3 |
| Kelzan ® S | 0.2 | 0.2 | 0.2 | 0.2 | 0.2 | 0.3 | 0.3 | 0.2 | 0.2 | 0.2 |
| Preventol ® D7 | 0.08 | 0.08 | 0.08 | 0.08 | 0.08 | 0.08 | 0.08 | 0.08 | 0.08 | 0.08 |
| Proxel ® GXL | 0.12 | 0.12 | 0.12 | 0.12 | 0.12 | 0.12 | 0.12 | 0.12 | 0.12 | 0.12 |
| Silfoam ® SRE | 0.1 | 0.1 | 0.1 | 0.1 | 0.1 | 0.1 | 0.1 | 0.1 | 0.1 | 0.1 |
| Citric acid | 0.1 | 0.1 | 0.1 | 0.1 | 0.1 | 0.1 | 0.1 | 0.1 | 0.2 | 0.2 |
| Water | 56.7 | 51.7 | 56.7 | 56.7 | 59.2 | 49.5 | 47 | 56.2 | 54.5 | 47.1 |

Comparative Examples

To prepare comparative examples comprising in each case only penetrant or adjuvant, initially all liquid components are mixed with one another. In the next step, the solids are added and the mixture is stirred until a homogeneous suspension is formed. The homogeneous suspension is subjected initially to coarse grinding and then to fine grinding, resulting in a suspension in which 90% of the solids particles have a particle size below 10 g/m. Subsequently, Kelzan® S and water are added at room temperature with stirring. This gives a homogeneous suspension concentrate.

TABLE 2

Compositions of the comparative formulations (in % by weight)

| | Comparative Example | |
|---|---|---|
| | 1 | 2 |
| Imidacloprid | 18.7 | 18.7 |
| Crovol ® CR 70 G | 10 | |
| Synergen ® GL 5 | | 5 |
| Glycerol | 10 | 5 |
| Emulgator PS ® 29 | 4 | 4 |
| Kelzan ® S | 0.6 | 0.2 |
| Preventol ® D7 | 0.08 | 0.08 |
| Proxel ® GXL | 0.12 | 0.12 |
| Silfoam ® SRE | 0.1 | 0.1 |
| Citric acid | 0.1 | 0.1 |
| Water | 56.3 | 66.7 |

Storage Stability of the Formulations According to the Invention

To examine the storage stability, 100 ml of formulation were stored under changing temperature conditions (TW) and at 54° C. for eight weeks. The changing temperature conditions are 48 hours at 30° C., reduction of the temperature over 22.5 hours at 2° C./hour to −15° C., 75 hours at −15° C., increase of the temperature over 5 hours at 2° C./hour to 30° C. After storage, the sample is brought to room temperature, and dispersibility, particle size and viscosity are checked.

The dispersibility (DISP) is determined according to the CIPAC MT 180 method, the particle size (d90, Part) is measured on a Malvern Mastersizer 2000, and the dynamic viscosity (Visc) is measured at 20 s$^{-1}$ using a RheoStress RS 150 from Haake.

TABLE 3

Storage stability of formulations according to the invention

| | Original value | | | 8 weeks at 54° C. | | | 8 weeks TW | | |
|---|---|---|---|---|---|---|---|---|---|
| | DISP in % | Part in μm | Visc/ mPas | DISP in % | Part in μm | Visc/ mPas | DISP in % | Part in μm | Visc/ mPas |
| Example 1 | 0 | 4.8 | 62 | 0 | 8.6 | 54 | 0 | 5.1 | 57 |
| Example 2 | 0.1 | 3.4 | 185 | 0.1 | 7.2 | 156 | 0.1 | 5.5 | 181 |
| Example 3 | 0.1 | 2.4 | 95 | 0.1 | 3.0 | 78 | 0.1 | 2.5 | 91 |
| Example 4 | 0.1 | 5.8 | 179 | 0.1 | 8.0 | 178 | 0.1 | 6.5 | 169 |

Determination of the Biological Action of Various Imidacloprid/Adjuvant Combinations This test measured the penetration of active compounds through enzymatically isolated cuticles of apple leaves.

The leaves used were cut in the fully developed state from apple trees of the Golden Delicious variety. The cuticles were isolated as follows:
- first of all, leaf discs labelled on the underside with dye and formed by punching were filled by means of vacuum infiltration with a pectinase solution (0.2% to 2% strength) buffered to a pH of between 3 and 4,
- then sodium azide was added and
- the leaf discs thus treated were left to stand until the original leaf structure broke down and the non-cellular cuticles underwent detachment.

Thereafter only those cuticles from the top leaf sides that were free from stomata and hairs were used further. They were washed a number of times in alternation with water and with a buffer solution, pH 7. The clean cuticles obtained were, finally, applied to Teflon plaques and smoothed and dried with a gentle jet of air.

In the next step the cuticular membranes obtained in this way were placed in stainless steel diffusion cells (transport chambers) for the purpose of membrane transport investigations. For these investigations the cuticles were placed centrally using tweezers on the edges of the diffusion cells, which were coated with silicone grease, and sealed with a ring, which was likewise greased. The arrangement was chosen so that the morphological outer side of the cuticles was directed outwards, in other words to the air, while the original inner side was facing the interior of the diffusion cell.

The diffusion cells were filled with a 1% phospholipid suspension. Penetration was determined by applying in each case 10 μl of the spray liquor of the composition below, containing radiolabelled active compound in the stated concentrations, to the outer face of the cuticles. The spray liquor is prepared using local mains water of average hardness.

After the spray liquors have been applied the water was evaporated and then the chambers were inverted and placed in thermostatted troughs, in which the temperature and air humidity over the cuticles was adjustable by means of a gentle air stream onto the cuticles with the spray covering (20° C., 60% rh). At regular intervals, an autosampler took aliquots which were subjected to measurement in a scintillation counter.

It was found that compositions according to the invention exhibit active compound penetration in a superadditive (synergistic) manner compared to the comparative examples where in each case only either penetrant or adjuvant is present.

TABLE 4

Synergistic activity of the formulations according to the invention

| | Penetration/% | | | | | |
|---|---|---|---|---|---|---|
| | (0.2 g imidacloprid/l) | | | (0.5 g imidacloprid/l) | | |
| | After 3 hours | After 9 hours | After 24 hours | After 3 hours | After 9 hours | After 24 hours |
| Example 1 | 6.9 | 18.3 | 33.5 | 4.4 | 14.5 | 27.3 |
| Comparative example 1 | 2.4 | 6.0 | 12.2 | 1.4 | 5.1 | 10.8 |
| Comparative example 2 | 1.1 | 3.0 | 5.7 | 1.8 | 5.4 | 10.0 |

Test Description: Penetrants on the Cuticle Level

Additives which act as penetrants on the level of the cuticles are referred to hereinbelow as accelerator additives (cf. Schönherr and Baur, 1994, Pesticide Science 42, 185-208). Accelerator additives are distinguished in that they penetrate from the aqueous spray liquor and/or the spray coating into the cuticles and are thus able to increase the mobility of active compounds in the cuticles. In contrast, other additives, such as polyethylene glycol, act only in the spray coating (via the liquid phase) or act only as a wetting agent, such as, for example, sodium dodecylsulphate.

In this test, the effect of additives on the penetration properties of other substances at the cuticle level is determined. Here, the mobility of a test substance in the cuticles is measured without and with an additive using a desorption method. The method is published in detail in the literature (Baur et al., 1997, Pesticide Science, 51, 131-152), and only the principles and modifications are described hereinbelow.

Here, the tracer test substance selected was a radiolabelled weak organic acid. The plant material used was enzymatically isolated leaf cuticles from the upper side of pear leaves of trees growing outdoors. The cuticles were mounted in specially designed stainless steel diffusion cells. The tracer was applied dissolved in a citrate buffer at pH 3 to the side originally orientated to the inside of the leaf. This inner side readily takes up the small radioactive amount of tracer in the non-dissociated acid form. This inner side was then covered and kept at 100% atmospheric humidity. The morphological outer side of the leaf cuticles, which is normally exposed to air, was then brought into contact with a buffer (pH 7), the receptor solution, and the desorption was started. The penetrated acid form of the test substance is dissociated by the receptor, and desorption takes place following first order kinetics. The desorption constant is proportional to the mobility of the tracer in the cuticles.

The invention claimed is:
1. Composition, comprising
   from 1 to 60% by weight of at least one systemic agrochemically active compound selected from the group consisting of imidacloprid, thiacloprid, and spirotetramate, from 1 to 50% by weight of at least one penetrant from the class of the polyalkoxytriglycerides obtainable by ethoxylation of rapeseed oil, the degree of ethoxylation being from 60 to 80% by weight, from 1 to 25% by weight of at least one adjuvant from the group of the polyglycerols or polyglycerol derivatives obtainable by copolymerization of
  a) glycerol,
  b) phthalic acid and
  c) coco acid, from 1 to 20% by weight of at least one nonionic surfactant and/or at least one anionic surfactant, and from 0.1 to 25% by weight of at least one additive selected from the group consisting of antifoams, preservatives, antioxidants, spreading agents, colorants and/or thickeners.

2. Composition according to claim 1, wherein the active compound comprises imidacloprid.

3. A method for controlling animal pests or phytopathogenic fungi, comprising applying an effective amount of the active compound of said composition according to claim 1 to animal pests, their habitat or plants.

4. Method for controlling animal pests or phytopathogenic fungi, comprising applying a composition according to claim 2 in diluted or undiluted form to animal pests, their habitat or plants such that an effective amount of the active compound comprised therein is applied.

5. Method for controlling animal pests or phytopathogenic fungi, comprising applying a composition according to claim 1 in diluted or undiluted form to animal pests, their habitat or plants such that an effective amount of the active compound comprised therein is applied.

6. Composition according to claim 1, wherein
the active compound is present in an amount of from 5 to 50% by weight,
the penetrant is present in an amount of from 2 to 30% by weight, and
the adjuvant is present in an amount of from 2 to 15% by weight.

7. Composition according to claim 1, wherein
the active compound is present in an amount of from 10 to 30% by weight,
the penetrant is present in an amount of from 5 to 20% by weight, and
the adjuvant is present in an amount of from 5 to 10% by weight.

8. Composition according to claim 1, wherein the active compound comprises spirotetramat.

9. Composition according to claim 1, wherein the active compound comprises thiacloprid.

10. Composition according to claim 1, wherein the active compound comprises imidacloprid and spirotetramat.

11. Composition according to claim 1, wherein the adjuvant comprises
19.9 to 99% by weight of structural units derived from the glycerol,
0.1 to 30% by weight of structural units derived from the phthalic acid, and
0.9 to 80% by weight of structural units derived from the coco acid.

12. Composition according to claim 1, wherein the adjuvant comprises
50 to 90% by weight of structural units derived from the glycerol,
1 to 25% by weight of structural units derived from the phthalic acid, and
2 to 49% by weight of structural units derived from the coco acid.

13. Composition according to claim 1, wherein the composition has a mean particle size of below 20 μm.

14. Composition according to claim 1, wherein the composition has a mean particle size of from 1 to 10 μm.

15. Composition according to claim 1, wherein the composition is a suspension concentrate.

* * * * *